United States Patent
Gervits et al.

(10) Patent No.: US 6,878,826 B2
(45) Date of Patent: Apr. 12, 2005

(54) PERFLUORONATED CYCLE-CONTAINING TERTIARY AMINES USED AS A BASIS FOR GAS-CONVEYING EMULSIONS AND DEVICE FOR THE PRODUCTION THEREOF

(75) Inventors: Lev Lvovich Gervits, Moscow (RU); Kirill Nikolaevich Makarov, Moscow (RU); Evgeny Ilich Maevsky, Puschino (RU); Genrikh Romanovich Ivanitsky, Puschino (RU); Sergei Jurievich Pushkin, Sadikovaya (RU); Igor Alexeevich Maslennikov, Moscow (RU)

(73) Assignee: Otkrytoe Aktsionernoe obschestvo Nauchno-proizvodstvennaya firma Perftoran, Moskovskaya Obl. (RU)

( * ) Notice: Subject to any disclaimer, the term of this patent is extended or adjusted under 35 U.S.C. 154(b) by 3 days.

(21) Appl. No.: 10/451,763
(22) PCT Filed: Dec. 29, 2000
(86) PCT No.: PCT/RU00/00547
§ 371 (c)(1), (2), (4) Date: Oct. 7, 2003
(87) PCT Pub. No.: WO02/053525
PCT Pub. Date: Jul. 11, 2002

(65) Prior Publication Data
US 2004/0054184 A1 Mar. 18, 2004

(51) Int. Cl.[7] ..................... C07D 207/04; C07D 211/06
(52) U.S. Cl. ......................................... 546/192; 548/400
(58) Field of Search .......................... 546/192; 548/400

(56) References Cited

U.S. PATENT DOCUMENTS

| | | | |
|---|---|---|---|
| 2,631,151 | A | 3/1953 | Kauck et al. |
| 5,214,214 | A | 5/1993 | Scherer, Jr. et al. |

FOREIGN PATENT DOCUMENTS

| | | |
|---|---|---|
| AU | 55002180 | 8/1981 |
| DE | 4 019 061 | 3/1991 |
| GB | 2 125 787 | 3/1984 |
| GB | 2 201 674 | 9/1988 |
| RU | 2 088 217 | 8/1997 |

OTHER PUBLICATIONS

English Abstract of DE 4 019 061 Dated: Mar. 7, 1991.
English Abstract of RU 2 088 217 Dated: Aug. 27, 1997.
Vorobyev, S.I., et al. "Perfluorocarbon Emulsions Stabilized with Nonionogenic Block Copolymers" "Collection of Papers" Perfluorocarbon Active Media for Medicine and Biology (New Aspects of Research) Push Chino, (1983) pp 33–46 with English Translation.

Ivanitskii, G.R., et al. "Life of Perfluorocarbon Emulsion" In Physiological Activity of Fluorine–Containing Compounds (Experiments and Clinical Tests) Push Chino (1995) pp 5–32 with English Translation.

Primary Examiner—Taofiq Solola
(74) Attorney, Agent, or Firm—Ladas & Parry LLP

(57) ABSTRACT

Tertiary perfluorocycloamines (TPFCAs) of general formula (1)

$$CF_3-CF\begin{matrix}(CF_2)_n\\ \\ CF_2-CF_2\end{matrix}CF-X \quad (1)$$

Figure 1:
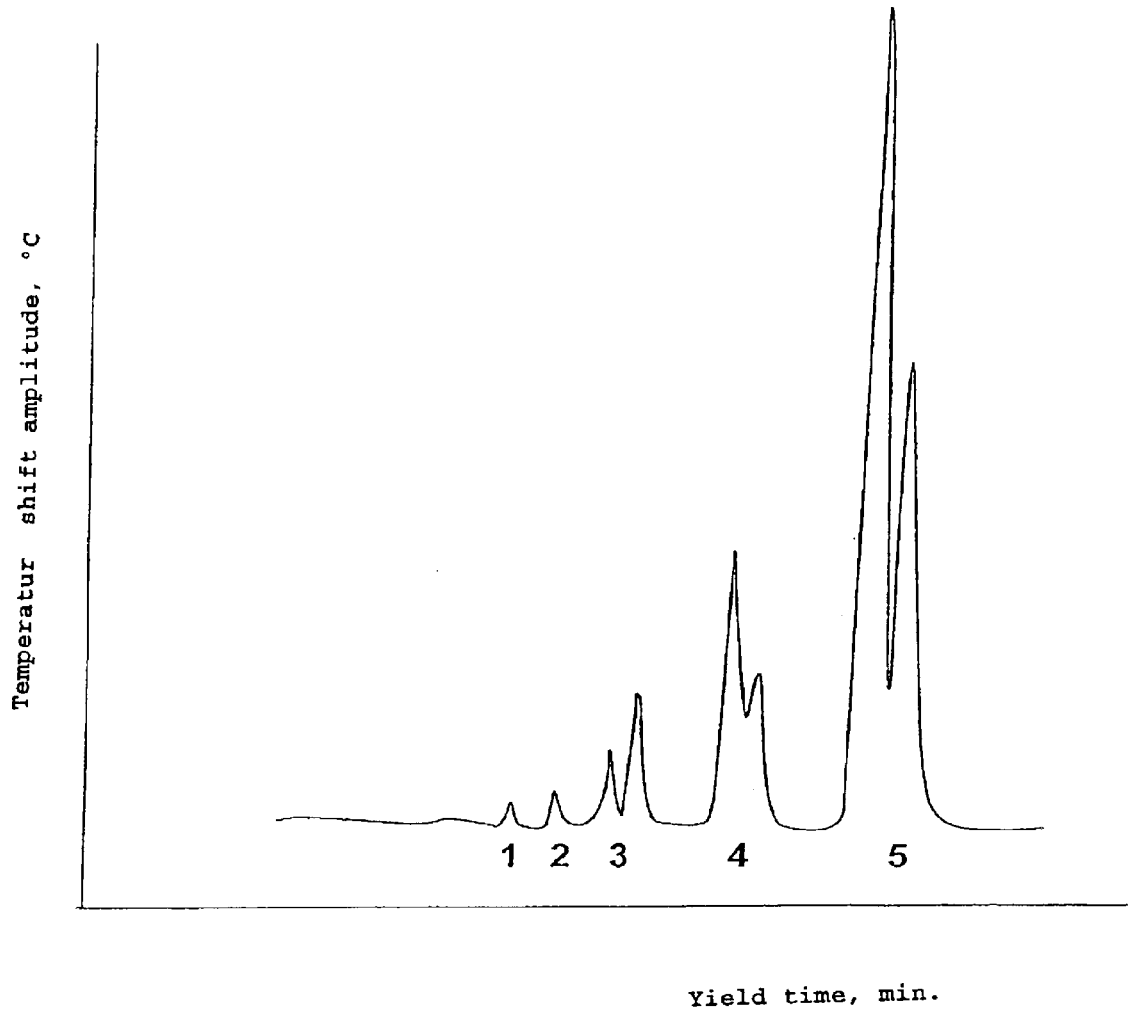

where n=1 or 2, m=2 or 3, X is $$-N\begin{matrix}CF_3\\ \\ (CF_2)_mCF_3\end{matrix} \quad \text{or} \quad -N\begin{matrix}(CF_2)_n\\ \\ CF_2-CF_2\end{matrix}CF-CF_3,$$

wherein at n=2 X is $$-N\begin{matrix}(CF_2)_n\\ \\ CF_2-CF_2\end{matrix}CF-CF_3$$

as the basis for gas transport emulsions.

TPFCAs comprise a group of compounds which are close in their physicochemical properties to perfluoro-N-(4-methyl-cyclohexyl)-piperidine, particularly in the critical temperature of dissolution in hexane, and which are used in a mixture, forming a number of compounds with gradually varying characteristics. Owing to this, a greater homogeneity of the fluorocarbon phase is achievable in the emulsions and it becomes possible to enhance the stability of the emulsion particles stabilized by an ethylene oxide-propylene oxide block copolymer, with the absence of toxicity for large animals. A mixture of TPFCAs is prepared by electrochemical fluorination of n-piperidinoheptafluorotoluene in anhydrous hydrogen fluoride. The use of this mixture of TPFCAs instead of individual perfluoro-N-(4-methylcyclohexyl) piperidine simplifies, speeds up the process for preparing perfluorinated organic compounds, makes it cheaper, and provides conditions for broader application of gas transport emulsions based thereon.

3 Claims, 1 Drawing Sheet

PERFLUORONATED CYCLE-CONTAINING TERTIARY AMINES USED AS A BASIS FOR GAS-CONVEYING EMULSIONS AND DEVICE FOR THE PRODUCTION THEREOF

FIELD OF THE ART

The present invention relates to the chemistry of fluororganic compounds and more particularly to a group of new tertiary perfluorocycloamines (TPFCA). The invention may be used most effectively as a basis for producing gas transport media intended for the preservation of organs, blood substitution and treating pathologies associated with regional blood flow disturbances.

STATE OF THE ART

Known in the art is a tertiary perfluorocycloamine, perfluoro-N-(4-methylcyclohexyl)-piperidine, which has the formula

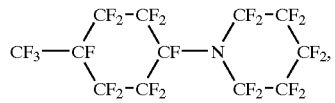

possesses lipophobic properties and is used as a basis for gas transport media both singly and in combination with lipophilic perfluororganic compounds (PFOCs), for instance, with perfluorodecalin (PFD) [see S. I. Vorobyev, G. R. Ivanitskij, K. N. Makarov, V. V. Moroz, V. P. Kutyshenko// Perfluorocarbon Emulsions Stabilized with Nonionogenic Block Copolymers//in: Collection of Papers "Perfluorocarbon Active Media for Medicine and Biology (New Aspects of Research)", Pushchino, 1993, pp. 33–46 (in Russian)].

In the specification to RU 2088217 published in the Bulletin "Izobreteniya . . . (Zayavki . . . ,)" No. 24, 27.08.1998 it is shown that introducing a lipophilic TPFCA perfluoro-N-(4-methylcyclohexyl)-piperidine into the formulation of the lipophilic fluorocarbon phase provides the elimination of toxicity in emulsions for large animals, this toxicity being typical of gas transport emulsions containing lipophilic rapidly eliminable PFOCs. However, in spite of all positive properties of emulsions prepared on the basis of lipophilic PFOCs and lipophobic perfluoro-N-(4-methylcyclohexyl)-piperidine, particles of such an emulsion are insufficiently stable. Their instability under freezing and thawing conditions during storage and when getting into the blood flow is caused, according to calculations and model experiments [G. R. Ivanitskij, S. I. Vorobyev, A. A. Deev// "Life" of Perfluorocarbon Emulsion//in: Collection of Papers "Physiological Activity of Fluorine-Containing Compounds (Experiments and Clinical Tests)", Pushchino, 1995, pp. 5–32 (in Russian)], by that PFOCs sharply differing in the lipophilicity, particularly in the temperature of critical dissolution in hexane, form heterogeneous clustered structures in the fluorocarbon phase, that are characterized by permanent turbulent motion within the emulsion particles, the stability of the adsorption layer of the surface active component being thus disturbed.

Besides, the preparation of perfluoro-N-(4-methylcyclohexyl)-piperidine is a highly labor-consuming and therefore costly process, so that using this compound individually involves difficulties. These factors taken together impose essential limitations on the commercial preparation of this compound an on a wide use of gas transport media for biomedical purposes.

ESSENCE OF THE INVENTION

It is an object of the present invention to provide new tertiary perfluorocycloamines close in their physicochemical and biological properties to perfluoro-N-(4-methylcyclohexyl)-piperidine, non-toxic for large animals, and improving the stability of emulsions under freezing and thawing conditions and upon getting into the blood flow, Another object of the invention is to simplify and speed-up the technological process of preparing TPFCAs suitable for use as a basis for the production of gas transport media and displaying an improved complex of useful properties.

Said objects are accomplished by using as the basis for gas transport emulsions a group of tertiary perfluorocycloamines of general formula (1)

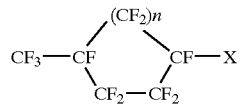

where n=1 or 2, m=2 or 3, X is

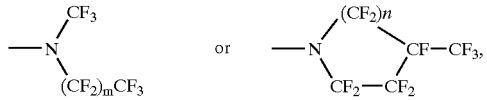

wherein at n=2 X is

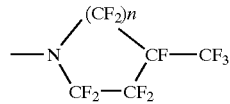

Said group of compounds is prepared by the electrochemical fluorination of n-piperidinoheptafluorotoluene. This group contains compounds having close physicochemical properties which provide their successful use in a mixture:

two isomers of perfluoromethylpropyl(methylcyclopentyl)-amine,
cis/trans-perfluoromethylpropyl(methylcyclohexyl)amine,
perfluoromethylbutyl-(4-methylcyclohexyl)amine,
cis/trans-perfluoro-N-(4-methylcyclohexyl)-2-methylpyrrolidine,
cis/trans-perfluoro-N-(4-methylcyclohexyl)-piperidine.

The critical parameter decisive for the possibility of using the products of the electrochemical fluorination of n-piperidinoheptafluorotoluene is the absence of underfluorinated products: hydrogen-containing or unsaturated compounds responsible for toxicity. In terms of toxicity parameters, the individual perfluoro-N-(4-methylcyclohexyl)-piperidine and a mixture of TPFCAs practically coincide both in the form of liquids and in the formulation of emulsions (Tables 1, 2).

All compounds of this group of TPFCAs are close in the lipophilic-lipophobic properties and in the critical temperature of dissolution in hexane (CTDH in the range of 34–30° C. with dissolution of 25 mol. %). In a mixture they form a number of compounds with gradually varying characteristics. Owing to this, a greater homogeneity of the fluorocarbon phase is achievable both in emulsions based on this group of compounds only and on a combination thereof with lipophilic perfluororganic compounds. Thereby it becomes possible to enhance the stability of the adsorption layer of the emulsion particles stabilized by an ethylene oxide-propylene oxide block copolymer (Table 3). The emulsions based on the TPFCA group, similarly to the emulsions containing individual perfluoro-N-(4-methylcyclohexyl)-piperidine, are not toxic for large animals (Table 2). In addition, these emulsions display a better complex of properties manifested in a greater stability of the prepared emulsions (Table 3). All this makes these emulsions suitable for use as perfusion media and blood-substituting compositions.

The electrochemical fluorination is carried out in an electrolytic cell charged with an electrolyte containing 10–25% of the starting n-piperidinoheptafluorotoluene in anhydrous hydrogen fluoride. The temperature is maintained in the range of 20–25° C. The current density is varied from 200 to 400 A/m² at 5–6 V. The process is run for 10–12 hours with periodic replenishing the reaction mixture with a more concentrated solution of the starting substance in anhydrous hydrogen fluoride. Depending on the reaction conditions, the yield of the fluorination products is from 61 to 78% of the starting product. After the removal of underfluorinated (hydrogen-containing and unsaturated) products a number of tertiary perfluorocycloamines are obtained with a boiling point within 179–196° C.

All the compounds are identified by chromatographic mass spectrometry and NMR spectrometry techniques. The main compound of the group of interest is cis/trans-perfluoro-N-(4-methylcyclohexyl)-piperidine (with the yield of 60% to 70%). Other TPFCAs are products of partial degradation and isomerization of the starting substance in the course of the electrochemical fluorination. Variations in the percentage of compounds in the TPFCA mixture upon variations of the cis/trans-perfluoro-N-(4-methylcyclohexyl)-piperidine content within the range of 60% to 70% do not tell in any substantial manner on the physicochemical and biological parameters of the obtained emulsions. A typical chromatogram of the prepared tertiary perfluorocycloamines is shown in FIG. 1 (capillary column, squalane, 100 m).

The described process for the preparation of TPFCA is much simpler and cheaper then the preparation of individual pure perfluoro-N-(4-methylcyclohexyl)-piperidine, whatever process for the preparation of the latter is used, because the above-described process does not require carrying out such labor-consuming procedures as preparative chromatography and rectification. The process for the preparation of individual perfluoro-N-(4-methylcyclohexyl)-piperidine is not described in the literature. Nevertheless, according to our estimates, the elimination from the process of the preparative chromatography and rectification operations, inevitable in isolating the individual products, makes the process several-fold simpler, faster and cheaper.

Said TPFCA mixture is used instead of individual perfluoro-N-(4-methylcyclohexyl)-piperidine for the preparation of gas transport emulsions. The simplified technology of the process makes it possible to contract expenses for the production of TPFCAs and thereby to reduce the production costs of gas transport media with a simultaneous enhancement of the stability and rheological properties of these media. All this opens up prospects for the commercial production and broader use of emulsions of perfluororganic compounds in research and clinical practice.

The present invention will be further illustrated by an example of preparing particular TPFCAs, this example being intended only for supporting the possibility of carrying out the invention, but not for limiting the Applicant's claims reflected in the set of claims hereinbelow.

BRIEF DESCRIPTION OF FIG. 1

FIG. 1 is a chromatogram of the prepared mixture of tertiary perfluorocycloamines (capillary column, squalane, 100 m), which shows the temperature shift amplitude determined with the help of a catharometric sensor vs. the substance yield time:

peak 1. two isomers of perfluoromethylpropyl (methylcyclo-pentyl)amine, peak 2. cis/trans-perfluoromethylpropyl (methylcyclohexyl)amine, peak 3. perfluoromethylbutyl-(4-methylcyclohexyl) amine, peak 4. cis/trans-perfluoro-N-(4-methylcyclohexyl)-2-methylpyrrolidine, peak 5. cis/trans-perfluoro-N-(4-methylcyclohexyl)-piperidine.

EXAMPLE 1

Preparation of Tertiary Perfluorocycloamines (TPFCAs)

A 2-liter electrolytic cell with external circulation of the electrolyte, provided with nickel electrodes having an area of 3000 cm², was charged with 1500 ml of an electrolyte containing 10% of n-piperidinoheptafluorotoluene in anhydrous hydrogen fluoride. The process of electrochemical fluorination was carried out at the temperature of 22° C., initial current density of 200 A/m² and voltage of 5 V. An electrolyte containing 60% solution of n-piperidinoheptafluorotoluene in anhydrous hydrogen fluoride was added periodically. During 10 hours of the fluorination the current density was increased gradually to 400 A/m² by increasing the voltage to 6 V. The total amount of the current passed was 800 Ah, and 330 g of n-piperidino-heptafluorotoluene were introduced into the reaction. Liquid products of the fluorination were separated from the electrolyte, washed with water, and with sodium bicarbonate solution to remove HF. After removing underfluorinated admixtures, the mixture of fluorination products was distilled, and 388 g (61%) of completely fluorinated compounds having a boiling point within 179–196° C. were obtained. According to the NMR spectroscopy and mass spectrometry data, the obtained completely fluorinated tertiary cycloamines comprise five kinds of compounds: 1—isomers of perfluoromethylpropyl (methylcyclopentyl)amine (1%), 2—cis/trans-perfluoromethylpropyl(methylcyclohexyl)-amine, 3—perfluoromethylbutyl-(4-methylcyclo-hexyl)amine (2%), 4—cis/trans-perfluoro-N-(4-methylcyclo-hexyl)-2-methylpyrrolidine (25%), 5—cis/trans-perfluoro-N-(4-methylcyclohexyl)-piperidine (64%) (see the chromatogram in FIG. 1).

EXAMPLE 2

The Use of TPFCA

The completely fluorinated products obtained as described in Example 1 were used for preparing a submicron emulsion containing 10 vol. % of TPFCA, 3 wt. % of an ethylene oxide-propylene oxide block copolymer and an aqueous solution of salts isotonic to blood plasma (120 mM of MaCl, 10 Mm of $NaHCO_3$, 2 mM of $KH_2PO_4$, 5 mM of KCl, 2 mM of $CaCl_2$), with 10 mM of glucose, 1 mM of sodium succinate, 1 mM of sodium pyruvate, 1 mM of sodium 2-hydroxybutyrate (perfusate pH 7.40). With the help of the produced emulsion, an isolated dog kidney was perfused under recirculation normothermal conditions (1 liter of the perfusate per 40 g of the kidney). The vital activity of the organ was maintained for 24 hours, replacing the perfusion composition every 6 hours, without damage to cell membranes (without edema, without substantial growth of the capillary resistance, with the perfusate pH being preserved, and without a drop of the oxygen consumption rate).

EXAMPLE 3

The Use of TPFCA

A mixture of the TPFCAs prepared as described in Example 1 with perfluorodecalin in a 1:2 ratio was used for preparing a submicron emulsion containing 10 vol. % of a fluorocarbon phase, 4 wt. % of an ethylene oxide-propylene oxide block copolymer, and an aqueous solution of salts isotonic to blood plasma (120 mM of NaCl, 8 mM of $NaHCO_3$, 1.2 mM of $KH_2PO_4$, 5 mM KCl), with 10 mM of glucose. The obtained emulsion was used for isovolumetric substitution of 65% of the volume of circulating blood in 10 rats under general anesthesia with premedication, with oxygen-enriched air being supplied to the animals for breathing in the course of the operation and during the first 24 hours after the blood substitution. All the animals which have undergone blood substitution, survived.

EXAMPLE 4

The Use of TPFCA

TPFCA in a mixture with perfluorodecalin were used for the preparation of a submicron emulsion as described in Example 3. The prepared emulsion was administered intravenously to ten 2.5–3.5 kg bodyweight rabbits in a dosage of 20 ml per kg. The deviation of the body temperature in the rabbits after the administration of the emulsion did not exceed 0.3° C. No symptoms of allergic reactions were observed. The content of leukocytes in the peripheral blood lowered by not more than 5% of the initial one, this being also indicative of the preparation being not reactogenic. All the rabbits successfully survived the critical period of 80 days (the period during which all the rabbits die, if an emulsion of pure perfluorodecalin is administered to them). No pathological abnormalities were found in the animals throughout the follow-up period (of more than 1 year).

TABLE 1

Comparison of the toxicity* of individual perfluoro-N-(4-methylcyclohexyl)-piperidine (PFMCP) and of a mixture of tertiary perfluorocycloamines (TPFCAs), and of emulsions based thereon

| Kind of investigated preparation (IP) | Culture medium/IP ratio | Concentration of fluorine ions ($10^{-6}$ M) | Percentage gain in cell growth after cultivation |
|---|---|---|---|
| Culture medium | — | 1.0 | 100% |
| Mixture of PFD and individual PFMCP | 20:1 | 1.0 | 90 ± 15% |
| Mixture of PFD and TPFCA | 20:1 | 1.0 | 90 ± 17% |
| Emulsion based on individual PFMCP | 10:1 | 5.5 | 65–95% |
| Emulsion based on TPFCA | 10:1 | 5.5 | 65–95% |

*Toxicity of perfluororganic compounds was assessed by the inhibition of the growth of cultivatd transformed lymphoid Raji line cells.

TABLE 2

Comparison of the toxicity of different PFOC emulsions in terms of the half-lethal dose for mice and of the survival of rabbits

| Kind of investigated preparation | Acute toxicity for mice, $LD_{50}$, in ml per kg | Survival of rabbits (in %) one year after the intravenous administration of the investigated preparations in dosage of 20 ml per kg bodyweight |
|---|---|---|
| Emulsion based on individual PFMCP | 140 | 100.0 |
| Emulsion based on individual PFD | 150 | 0.0 |
| Emulsion based on PFD and individual PFMCP (2:1 ratio) | 140 | 100.0 |
| Emulsion based on PFD and TPFCA (2:1 ratio) | 140 | 100.0 |

TABLE 3

Comparison of the stability of PFD/PFMCP- and PFD/TPFCA-based emulsion

| Kind of perfluororganic compounds entering into the formulation of emulsions | Enlargement of the mean particle size with the initial size thereof of 0.08 μm | | Optical density after mixing the emulsion with different concentrations of dextran in the 1:1 ratio | | |
|---|---|---|---|---|---|
| | After 45 days of storage at 4° C. | After 5-fold freezing and thawing | Without dextran | 3% dextran | 6% dextran |
| PFD and PFMCP in 2:1 ratio | 0.14 ± 0.01 | 0.15 ± 0.02 | 0.10 | 0.35 | 0.88 |
| PFD and TPFCA in 2:1 ratio | 0.12 ± 0.01 | 0.11 ± 0.01 | 0.10 | 0.19 | 0.62 |

What is claimed is:

1. Tertiary perfluorocycloamines of general formula (1)

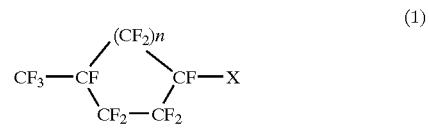

(1)

where n=1 or 2, m=2 or 3, X is

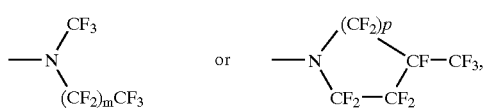

wherein at n=2
as the basis for gas transport emulsions.

2. Tertiary perfluorocycloamines according to claim 1, selected from two isomers of perfluoromethylpropyl-(methylcyclo-pentyl)amine; cis/trans-perfluoromethylpropyl(4-methylcyclo-hexyl)amine; perfluoromethylbutyl-(4-methylcyclohexyl)amine; cis/ trans-perfluoro-N-(4-methylcyclohexyl)-2-methylpyrrolidine; cis/trans-perfluoro-N-(4-methylhexyl)-piperidine, displaying close physicochemical properties and used in a mixture.

3. A process for the preparation of tertiary perfluorocycloamines of general formula (1)

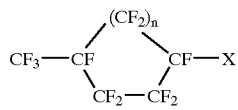

where n=1 or 2, m=2 or 3, X is

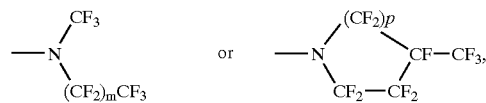

wherein at n=2 comprising electrochemical fluorination of a starting product in anhydrous hydrogen fluoride, characterized in that said starting product subjected to the electrochemical fluorination is n-piperidinoheptafluorotoluene.

* * * * *